(12) United States Patent
Devaux et al.

(10) Patent No.: US 8,609,893 B2
(45) Date of Patent: Dec. 17, 2013

(54) PROCESS FOR MANUFACTURING ACROLEIN AND/OR ACRYLIC ACID FROM GLYCEROL

(75) Inventors: Jean-Francois Devaux, Soucieu En Jarrest (FR); Andre Lozowski, Lescar (FR); Nabil Tlili, Mulhouse (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/515,060

(22) PCT Filed: Dec. 10, 2010

(86) PCT No.: PCT/FR2010/052668
§ 371 (c)(1),
(2), (4) Date: Sep. 12, 2012

(87) PCT Pub. No.: WO2011/073552
PCT Pub. Date: Jun. 23, 2011

(65) Prior Publication Data
US 2012/0330058 A1    Dec. 27, 2012

Related U.S. Application Data

(60) Provisional application No. 61/314,237, filed on Mar. 16, 2010.

(30) Foreign Application Priority Data

Dec. 14, 2009  (FR) ...................................... 09 58947

(51) Int. Cl.
*C07C 51/50*    (2006.01)

(52) U.S. Cl.
USPC .......................................................... 562/513

(58) Field of Classification Search
USPC .......................................................... 562/513
See application file for complete search history.

(56) References Cited

U.S. PATENT DOCUMENTS

| 6,348,638 B1 | 2/2002 | Schliephake et al. |
| 2009/0134357 A1 | 5/2009 | Bub et al. |
| 2010/0168471 A1 | 7/2010 | Dubois |

OTHER PUBLICATIONS

Studies in Surface Science and Catalysis vol. 51—New Solid Acids and Bases; Their Catalytic Properties—Kozo Tanabe, Makoto Misono, Yoshio Ono, Hideshi Hattori—pp. 1-24.
Daniel Ballerini et Gerard Hillion—Pactualite Chimique Nov./Dec. 2002 "Methanolysis of Vegetable Oils" (6 Pages).

*Primary Examiner* — Nizal Chandrakumar
(74) *Attorney, Agent, or Firm* — Lynn B. Morreale (57) ABSTRACT

The present invention relates to the manufacture of bioresourced acrolein and bioresourced acrylic acid from glycerol as starting material and more particularly comes within the scope of a process for the manufacture of acrolein and acrylic acid according to which the reaction for the dehydration of glycerol to give acrolein is carried out and the organic compounds which are heavier than water liable to be present in the various streams of the process arc removed, so as to obtain a stream which can be recycled to the dehydration stage without accumulation of heavy impurities, while minimizing the consumption of water and the discharge of polluted aqueous streams.

11 Claims, 4 Drawing Sheets

PROCESS FOR MANUFACTURING ACROLEIN AND/OR ACRYLIC ACID FROM GLYCEROL

CROSS-REFERENCE TO RELATED APPLICATIONS

This application is claims benefit to FR application FR 09.58947, filed Dec. 14, 2009, PCT/FR10/52668, filled Dec. 10, 2010, and U.S. Ser. No. 61/314,237, filed Mar. 16, 2010 which are hereby incorporated by reference in their entireties.

FIELD OF THE INVENTION

The present invention relates to the manufacture of bioresourced acrolein and bioresourced acrylic acid from glycerol as starting material and more particularly comes within the scope of a process for the manufacture of acrolein and acrylic acid according to which the reaction for the dehydration of glycerol to give acrolein is carried out and the organic compounds which are heavier than water liable to be present in the various streams of the process are removed, so as to obtain a stream which can be recycled to the dehydration stage without accumulation of heavy impurities, while minimizing the consumption of water and the discharge of polluted aqueous streams.

PRIOR ART

The process for the synthesis of acrylic acid most widely employed industrially uses a catalytic reaction of propylene using an oxygen-comprising mixture. This reaction is generally carried out in the vapour phase and generally in two stages: the first stage carries out the substantially quantitative oxidation of the propylene to give an acrolein-rich mixture in which acrylic acid is a minor component and then the second stage carries out the selective oxidation of the acrolein to give acrylic acid. The reaction conditions of these two stages, carried out in two reactors in series or in the two reaction regions of a single reactor, are different and require catalysts suited to each of the reactions.

For some years, manufacturers have been carrying out research and development studies on processes for the synthesis of acrolein and acrylic acid using bioresourced starting materials. These studies arise from concern to avoid the use in the future of fossil starting materials, such as propylene, the petroleum origin of which is contributing to global warming due to the greenhouse effect. Furthermore, its cost can only increase in the future with the decline in global oil reserves.

Mention may be made, among these alternative processes starting from non-fossil starting materials, of the processes using, as starting material, 3-hydroxypropionic acid obtained by fermentation of glucose or molasses originating from biomass.

Mention may also be made of the processes starting from glycerol (also known as glycerin) resulting from the methanolysis of vegetable or animal oils at the same time as the methyl esters, which are themselves employed in particular as fuels in gas oil and domestic heating oil. This glycerol is a natural product which enjoys a "green" aura, it is available in large amounts and it can be stored and transported without difficulty. The methanolysis of vegetable oils or animal fats can be carried out according to various well known processes, in particular by using a homogenous catalysis, such as sodium hydroxide or sodium methoxide in solution in methanol, or by using a heterogeneous catalysis. Reference may be made on this subject to the paper by D. Ballerini et al. in l'Actualité Chimique of November-December 2002.

The processes using 3-hydroxypropionic acid as starting material have a major disadvantage from an economic viewpoint. They involve a fermentation reaction which is necessarily carried out under highly dilute conditions in water. In order to obtain acrylic acid, a very large amount of water has to be removed by distillation, at the price of a very high energy cost. Furthermore, the energy expended to separate the water, which energy is produced from fossil material, will be highly damaging to the initial advantage of producing acrylic acid from this bioresourced starting material. Mention may be made, in this field, of Application WO 2006/092271, which describes a process for the production of polymers from acrylic acid prepared by the enzymatic route, in particular from carbohydrate.

Glycerol is recognized today as suitable starting material for envisaging the industrial manufacture of bioresourced acrolein and bioresourced acrylic acid.

The reaction involved in order to obtain acrolein from glycerol is:

This stage is followed by an oxidation of the acrolein in order to obtain the acrylic acid.

Various processes for the synthesis of acrolein from glycerol are described in the literature. Mention may be made of the documents FR 695 931, U.S. Pat. No. 2,558,520, WO 99/05085, U.S. Pat. No. 5,387,720, WO 06/087083, WO 06/087084 and WO 09/044081.

In Patent Application EP 1 710 227, the reaction product resulting from the reaction for the dehydration of glycerol in the gas phase is subjected to a subsequent stage of oxidation in the gas phase in order to obtain acrylic acid. The process is carried out in two reactors in series, each comprising a catalyst suited to the reaction being carried out. It is recommended to add oxygen to the gas mixture feeding the second reactor, in order to improve the oxidation reaction and to obtain the acrylic acid with a high yield. This two-stage process is carried out with pure glycerol or with aqueous solutions comprising more than 50% by weight of glycerol. It is advisable to use a concentrated glycerol solution in order to limit the energy cost related to the evaporation of the aqueous solution and the cost related to the treatment of the waste water. However, if the concentration of glycerol is too high, there is a risk that more side reactions will take place, resulting in numerous by-products, such as the formation of glycerol ethers or reactions between the acrolein produced or the acrylic acid produced and the glycerol. These heavy by-products have a tendency to remain on the dehydration catalyst and they result in coking of the catalyst and in its very rapid deactivation.

Application WO 06/136336 describes a process for the synthesis of acrolein and acrylic acid in which the dehydration reaction is followed by a stage of separation into an acrolein-rich phase and an acrolein-poor phase, the latter phase, which is rich in water, being returned upstream of the dehydration reactor in order to dilute the glycerol and to obtain an aqueous phase comprising less than 10% of glycerol.

In this Application WO 06/136336, which relates essentially to a liquid-phase dehydration process, the acrolein-poor and water-rich phase also comprises heavier compounds formed during the dehydration reaction which have a tendency to form, in the reaction stage, heavy compounds which foul the catalyst and bring about its deactivation.

International Application WO 2006/092272 describes a process for the preparation of acrylic acid from glycerol comprising either a stage of dehydration of the glycerol in the liquid phase or a stage of dehydration in the gas phase. The reaction mixture comprising the acrolein obtained from the reaction for the dehydration of the glycerol is brought into contact with water in a quench unit before being sent to the oxidation reactor. In the presence of a large stream of water, there is a risk that the catalyst for the oxidation of acrolein will rapidly lose its effectiveness and its mechanical strength, making it difficult to maintain such a process. According to FIG. 5 of this document, the reaction mixture resulting from the liquid-phase dehydration is subjected to a distillation which separates, on the one hand, the light products with a boiling point lower than that of the acrolein and, on the other hand, a fraction comprising the heavy products with a boiling point greater than that of the acrolein, this second fraction, which is rich in water, being returned to the reaction stage after having removed the impurities in a separator equipped with a membrane. The principle of such a recycling can nevertheless result in the accumulation of some impurities in the water loop thus generated, due to the lack of selectivity of the membrane or to the fouling thereof.

Application WO 08/087315 describes a process for the preparation of acrylic acid from glycerol in two stages, in which use is made of an intermediate stage consisting in condensing, at least in part, the water and the heavy by-products present in the stream resulting from the first dehydration stage, before sending the stream to the oxidation reactor. This process makes possible the use of dilute aqueous glycerol solutions, producing a beneficial effect on the dehydration reaction, while limiting possible damage to the catalyst for the oxidation of acrolein in the presence of an excessively large amount of water. The aqueous stream thus generated by the condensation stage is sent, in all or in part, either to a rectification column, in order to recover the light products possibly present, or to a part for the treatment of waste water, however exhibiting the disadvantage of expensive treatments before discharge to the natural environment of large amounts of aqueous effluents. Alternatively, this stream can be sent to a thermal oxidizer where it is incinerated, or also a portion of this stream can be directly recycled in order to dilute the glycerol to the desired concentration, in which case impurities may accumulate in the water loop thus formed and the risk may exist of coking of the dehydration catalyst.

The present invention proposes to overcome the disadvantages exhibited by the abovementioned processes for the manufacture of acrylic acid in order to significantly improve the process for the manufacture of acrylic acid, comprising a first stage of dehydration of glycerol to give acrolein, followed by a stage of oxidation of the acrolein to give acrylic acid, with regard to the following points:
  reduction in the consumption of water, while ensuring optimization of the reaction for the dehydration of glycerol in the presence of water,
  limitation of polluted aqueous discharges,
  reduction in the energy consumption and in the size of the installations,
  limitation of the losses of product while ensuring efficient recovery of the reaction products,
  increase in the cycle period of the dehydration and oxidation catalysts.

To this end, it is proposed to separate the heavy by-products, in particular the organic compounds which are heavier than water, liable to be present in the various streams of the process, so as to obtain a stream which can be recycled to the dehydration stage which is as free as possible from these heavy impurities. The separation of the heavy impurities is carried out by difference in boiling points and can be carried out at different places in the process, which makes it possible to generate a closed water loop in the process without accumulation of heavy impurities and with energy optimization of the system.

SUMMARY OF THE INVENTION

A subject-matter of the present invention is thus a process for the manufacture of acrolein from glycerol comprising at least the following stages:
a) glycerol is subjected to a dehydration reaction in order to obtain an aqueous stream comprising acrolein,
b) the stream resulting from stage a) is separated into an acrolein-rich phase and an acrolein-poor aqueous phase,
c) all or part of the acrolein-poor aqueous phase is recycled to stage a), characterized in that a stage of separation of heavy by-products by difference in boiling point is carried out, which stage is applied to one at least of the following streams the stream entering stage a), the aqueous stream exiting from stage a) or the acrolein-poor aqueous phase of stage b).

Another subject-matter of the invention is a process for the manufacture of acrylic acid from glycerol comprising at least the following stages:
a) glycerol is subjected to a dehydration reaction in order to obtain an aqueous stream comprising acrolein,
b) the stream resulting from stage a) is separated into an acrolein-rich phase and an acrolein-poor aqueous phase,
c) all or part of the acrolein-poor aqueous phase is recycled to stage a),
d) the acrolein-rich phase is subjected to a catalytic oxidation reaction in order to Obtain a stream comprising acrylic acid,
e) the stream resulting from stage d) is subjected to one or more purification treatments and purified acrylic acid is recovered,
characterized in that a stage of separation of heavy by-products by difference in boiling point is carried out, which stage is applied to one at least of the following streams: the stream entering stage a), the aqueous stream exiting from stage a) or the acrolein-poor aqueous phase of stage b).

In a preferred embodiment of the invention, a stage of separation of the heavy by-products by difference in boiling point is applied to the stream entering stage a) and/or to the acrolein-poor aqueous phase of stage b), in combination or not in combination with a stage of separation of heavy by-products by difference in boiling point applied to the aqueous stream exiting from stage a).

Other characteristics and advantages of the invention will more clearly emerge on reading the detailed description which follows and the nonlimiting implementational examples of the invention, with reference to the appended figures, which represent.

DETAILED DESCRIPTION OF THE INVENTION

Manufacture of Acrolein

Figure 1:
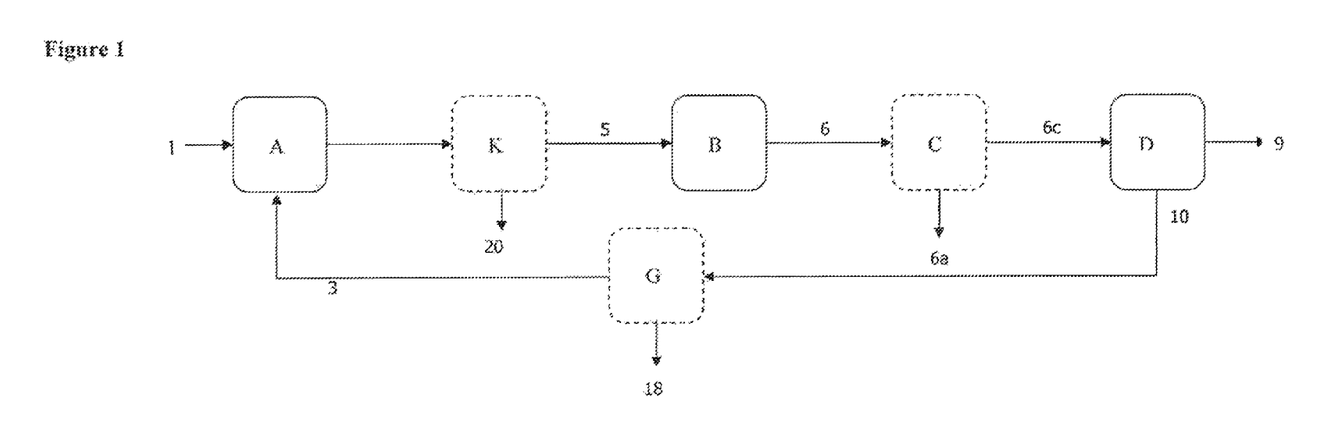
FIG. 1: block diagram of the process for the manufacture of acrolein according to the invention, in which the stage of separation of heavy by-products by difference in boiling point is represented in dotted lines.

FIG. 1 is a simplified representation of the process for the manufacture of acrolein according to the invention which indicates, in dotted lines, the various alternative forms possible for the stage of separation of the heavy by-products inserted into the block diagram of a process of the prior art.

With reference to FIG. 1, use is generally made, for feeding the reactor (B) of stage a) for dehydration of glycerol, of a stream (5) comprising the glycerol and water, with a water/glycerol ratio by weight which can vary within wide limits, for example between 0.04/1 and 9/1 and preferably between 0.7/1 and 5/1. The stream (5) can also comprise oxygen, nitrogen, argon, CO and $CO_2$.

This stream (5) is advantageously obtained during a stage of mixing (A) a stream (1) rich in glycerol and a phase (3) rich in recycled water which can comprise nitrogen, oxygen, glycerol or organic impurities from the process. The stream (1) can, for example, be crude commercial glycerol (glycerin), that is to say typically comprising 80-90% of glycerol, 1 to 10% of salts, 1 to 4% of non-glycerin organic matter, including methanol, and 3 to 15% of water. Use is advantageously made of desalted glycerol, which can be obtained from crude glycerol by any means known to a person skilled in the art, such as distillation under reduced pressure or flash distillation under reduced pressure or separation using ion-exchange resins, such as described, for example, in Application EP 1 978 009. It is also possible to start from salt-free glycerin obtained by processes for the transesterification of oils catalyzed by heterogeneous catalysts. It is also possible to use refined glycerin with a purity of greater than 98%, 99% or 99.5%. It is also possible to use an aqueous solution comprising from 20 to 99% by weight, preferably from 30 to 80% by weight, of glycerol.

The dehydration reaction, stage a), which is favoured by a high temperature level, is generally carried out in the gas phase in the reactor (B) in the presence of a catalyst at a temperature ranging from 150° C. to 500° C., preferably between 250° C. and 350° C., and at a pressure of between $10^5$ and $5 \times 10^5$ Pa (1 and 5 bar). It can also be carried out in the liquid phase; in this case, the temperature is between 150° C. and 350° C. under a pressure ranging from $5 \times 10^5$ to $100 \times 10^5$ Pa. Preferably, this first stage is carried out in the gas phase.

It is also possible to carry it out in the presence of oxygen or of a gas comprising oxygen, as described in Applications WO 06/087083 and WO06/114506. In this case, the amount of oxygen is chosen so as to be outside the flammability range at any point of the plant. The molar ratio of molecular oxygen to glycerol is generally of the order of 0.1 to 1.5, preferably of 0.3 to 1.0.

The dehydration reaction can also be carried out in a reaction medium comprising a gas phase comprising from 1 to 3000 ppm of a compound which is an acid within the meaning of the Pearson classification chosen, for example, from $SO_3$, $SO_2$ or $NO_2$, the dehydration reaction being carried out either in the gas phase or in the liquid phase.

The reaction for the dehydration of glycerol is generally carried out over solid acid catalysts. The catalysts which are suitable are homogeneous or multiphase substances which are insoluble in the reaction medium and which have a Hammett acidity, denoted. $H_0$, of less than +2. As indicated in U.S. Pat. No. 5,387,720, which refers to the paper by K. Tanabe et al. in "Studies in Surface Science and Catalysis", Vol. 51, 1989, chap. I and 2, the Hammett acidity is determined by amine titration using indicators or by adsorption of a base in the gas phase.

These catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts.

These catalysts can in particular be composed of a heteropolyacid salt in which the protons of the said heteropolyacid are exchanged with at least one cation chosen from elements belonging to Groups I to XVI of the Periodic Table of the Elements, these heteropolyacid salts comprising at least one element chosen from the group consisting of W, Mo and V.

Mention may particularly be made, among mixed oxides, of those based on iron and on phosphorus and of those based on caesium, phosphorus and tungsten.

The catalysts are chosen in particular from zeolites, Nation® composites (based on sulfonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulphate $SO_4$, tungstate $WO_3$, phosphate $PO_4$, silicate $SiO_2$ or molybdate $MoO_3$ functional groups, or a mixture of these compounds.

The preceding catalysts can additionally comprise a promoter, such as Au, Ag, Cu, Pt, Rh, Pd, Ru, Sm, Ce, Yt, Sc, La, Zn, Mg, Fe, Co, Ni or montmorillonite, The preferred catalysts are phosphated zirconias, tungstated zirconias, silica zirconias, titanium or tin oxides impregnated with tungstate or phosphotungstate or silicotungstate, phosphated aluminas or silicas, heteropolyacids or heteropolyacid salts, iron phosphates and iron phosphates comprising a promoter.

It is also possible to carry out the reaction from the dehydration of glycerol in the presence of an amount of hydrogen ranging from 0.1 to 10% by volume with respect to the reaction mixture and, in this case, in the presence of a catalyst chosen from those described in Application US 2008/018319.

The reactor (B) used can operate as a fixed bed, as a moving bed, as a fluidized bed or as a circulating fluidized bed or in a configuration as modules (sheets or pans). The contact time, expressed in seconds, is the ratio of the volume of the catalyst bed to the volume of the gaseous reactants conveyed per second. The average temperature and pressure conditions existing in a bed can vary according to the nature of the catalyst, the nature of the catalytic bed and the size of the catalyst. In general, the contact time is from 0.1 to 20 seconds and preferably from 0.3 to 15 seconds, On completion of stage a), an aqueous stream (6), which can be liquid or gaseous and which comprises the desired acrolein, water, unreacted glycerol and by-products, such as hydroxypropanone, propionaldehyde, acetaldehyde, formaldehyde, acrylic acid, propionic acid, acetic acid, formic acid, acetone, phenol, addition products of acrolein with glycerol, polycondensation products of glycerol or cyclic glycerol ethers, and also light compounds, such as nitrogen, oxygen, carbon monoxide and carbon dioxide, is obtained. Some of these products are heavy compounds and others are condensable light compounds. Others are light compounds which cannot be condensed under the temperature and pressure conditions normally employed.

The stream (6) has a high water content due to the composition of the stream (5) entering the reactor (glycerol charge) and to the reaction itself (dehydration). Stage b) in the process according to the invention consists in separating this stream (6) into a phase (9) enriched in acrolein and a phase (10) rich in water and depleted in acrolein. This stage b), such as the partial separation of the water described, for example, in Patent Application WO 08/087315 on behalf of the Applicant Company or such as the separation described in Application WO 2006/136336, has the aim of removing most of the water present and the heavy byproducts before sending the stream comprising the acrolein to a purification stage, in a process for the manufacture of acrolein, or to the stage for the oxidation of acrolein to give acrylic acid, in a two-stage process for the manufacture of acrylic acid from glycerol. This partial separation of the water thus makes it possible to avoid damage to the catalyst of the 2nd stage of the oxidation of acrolein to give acrylic acid and to avoid, during the subsequent stages, the removal of large amounts of water, which could well be expensive and result in losses of acrylic acid. In addition, it makes it possible to remove a portion of the "heavy" impurities formed during the dehydration of the glycerol.

This stage b) is carried out on a separating unit (D). In the case where stage a) was carried out in the gas phase, the separating unit (D) is a condensation plant which can comprise an absorption column coupled or not coupled to an evaporator, one or more heat exchangers, one or more condensers, a dephlegmator, and any item of equipment well known to a person skilled in the art which makes it possible to carry out a partial condensation of an aqueous stream. It is carried out under conditions such that from 20 to 95%, preferably from 40 to 90%, of the water present in the stream (6) is removed in the liquid stream (10). The gas stream (9) generally comprises more than 80% and preferably more than 90% of the acrolein initially present in the stream (6). This result is obtained by lowering the temperature to a temperature of 60 to 120° C.

In the case where stage a) was carried out in the liquid phase under pressure, stage b) can be carried out by a reduction in pressure to a pressure of 1 to 4 bar, optionally coupled to a heat exchanger and a gas/liquid separation plant which can be a flash drum, a distillation column or any other device known to a person skilled in the art. A liquid stream (10) is recovered which comprises from 20 to 95%, preferably from 40 to 90%, of the water present in the stream (6) and a gas stream (9) is recovered which comprises more than 80% and preferably more than 90% of the acrolein initially present in the stream (6).

The condensed phase (10) thus generated generally comprises from 90 to 99% of water, the remainder representing acrolein and impurities, such as acrylic acid, glycerol, acetic acid, hydroxypropanone, propionic acid and other organic compounds which are heavier than water.

One of the objects of the process of the invention is to obtain a water-rich and acrolein-poor aqueous phase (10) which can be recycled, at least in part, to the reaction stage in the form of a stream (3) devoid of heavy impurities harmful to the dehydration catalyst.

For this, a stage of removal of the organic compounds which are heavier than water is carried out, either at the level of the stream (5) entering the dehydration reactor (B), or on the aqueous stream (6) exiting from the dehydration reactor (B), or on the water-rich and acrolein-poor aqueous phase (10) exiting from the separating unit (D), it being possible for these alternative forms to be used alone or in combination. A closed loop of water is obtained, thus avoiding an excessively high consumption of water in the process.

The removal of the organic compounds heavier than water is carried out by difference in boiling points of these compounds, either by evaporation, when the stream to be separated is initially liquid, or by condensation, when the stream to he separated is initially gaseous, or by a combination of evaporation and of condensation, when several separation stages are used.

According to a first embodiment of the invention, the stage of removal of the heavy compounds is carried out by evaporation of the mixture of glycerol (1) and of the recycled water-rich phase (3) in a device (K), which generates a phase rich in glycerol and in water and depleted in heavy compounds (stream (5)), which is conveyed to the dehydration reactor (B), and a liquid or solid phase (20) rich in organic compounds heavier than water, which is eliminated.

According to a second embodiment of the invention, the stage of removal of the heavy compounds is carried out by a treatment of the stream (6) exiting from the dehydration reactor (B) in a device (C), which generates a gas phase (6c) depleted in organic compounds heavier than water and a liquid or solid phase (6a) enriched in organic compounds heavier than water, which is eliminated. In the case of a gas-phase dehydration reaction, the device (C) will cool the stream (6), so as to generate a liquid condensed phase (6a) and a gas phase (6c), in the case of a liquid-phase dehydration reaction, the device (C) will make it possible to partially evaporate the stream (6) by reduction in pressure or by heating to give a gas stream (6c) and a solid or liquid stream (6a).

According to a third embodiment of the invention, the stage of removal of the heavy compounds is carried out by evaporation of the stream (10) exiting from the separating unit (D) in a device (G), which generates a water-rich gas phase (3), which is recycled, and a liquid or solid phase (18) enriched in organic compounds heavier than water, which is eliminated.

Use may be made, as devices (K) and (G), of evaporators or distillation columns Any type of evaporator known to a person skilled in the art can be envisaged, such as jacketed evaporators, coil evaporators, horizontal, vertical or inclined tube evaporators, natural convection or forced circulation evaporators, agitated or wiped film evaporators or plate-type evaporators. It is also possible to use plate distillation columns or columns comprising structured or random packings. Advantageously, these columns comprise an evaporation or reboiling region over which heat can be introduced by any means known to a person skilled in the art, such as thermosiphon or forced circulation exchangers operating with steam or heating elements. These columns can comprise one or more cooling exchangers intended to produce reflux and to enhance the capabilities for separation of the heavier products than the water to be separated.

The devices (K) can have, in addition to their role of separating heavy products, the role of evaporating the glycerol. Attempts will advantageously be made to reduce the residence time and the wail temperature of the exchangers with which the glycerol/water mixture is in contact. Forced circulation may be advantageous. The operating temperature of the devices (K) will advantageously be around the boiling point of glycerol under the conditions of pressure and of composition of the plant, i.e. typically between 180° C. and 320° C. and preferably between 200° C. and 270° C. Advantageously, the devices (K) can comprise a section for stripping glycerol from heavy products, so as to avoid too much loss of glycerol.

The devices of type (G) will preferably operate in the vicinity of the boiling point of the water under the conditions of pressure and of composition of the incoming stream, i.e. typically from 100° C. to 180° C. and preferably from 110° C. to 150° C.

Use may be made, as devices (C), of a contactor composed of a empty column or a packed column having an external recirculation loop in which the liquid phase is withdrawn at the bottom of the said column, cooled in a cooling exchanger and returned at the top of the said column. In the case of a empty column, the cooled liquid phase will be sprayed at the top of the column so as to facilitate the exchanges of heat. The temperature of the said liquid phase will typically be from 120° C. to 1.80° C. and preferably from 140° C. to 170° C. Advantageously, the recirculation flow rate will be adjusted so as to obtain a small difference in temperature between the inlet and outlet of the cooling exchanger, typically of less than 30'C and preferably of less than 10° C.

The device (C) can also be composed of a thin layer exchanger, such as, for example, a wiped film exchanger.

The device (C) can also be composed of a multitubular exchanger comprising gas/liquid separation at the outlet.

Alternatively, a liquid can be added to the gas phase in one of the technical solutions presented above so as to increase the contact with the exchange surfaces. The choice will be made of a liquid with a boiling point greater than the operating point of the device (C), such as, for example, glycerol.

Advantageously, an exchanger will be placed on the gas phase between the outlet of the reactor (B) and the inlet of (C) which makes it possible to cool the gas phase without condensing and to recover heat. At the outlet of this exchanger, the temperature is typically from. 150° C. to 250° C. and preferably from 180° C. to 230° C.

In all the embodiments of the invention, a stream (3) is obtained which can advantageously be recycled, in all or in part, to the stage a) of dehydration of the glycerol, without risk of accumulation of impurities on the dehydration catalyst; this stream (3) makes it possible in particular to adjust the water content of the stream (5) comprising the glycerol which will, feed the dehydration reactor (B). Advantageously, the stream (3) can be superheated in order to make it possible to evaporate the glycerol stream in the mixing stage (A) before conveying the reactive gas stream to the dehydration reactor (B), thereby avoiding having to bring the glycerol into contact with a very hot wall, which is necessary in order to evaporate it, since all of the heat is contributed by the superheated stream (3).

The liquid or solid phases enriched in organic compounds heavier than water are either eliminated or conveyed to a thermal oxidizer for elimination of the compounds in the form of $CO_2$ and $H_2O$.

Insofar as the reaction for the dehydration of glycerol to give acrolein produces 2 molecules of water per molecule of acrolein produced, a bleed on the stream (3) can be provided so as to avoid the accumulation of water in the loop. This bled-off product can be eliminated, either directly or via a system for the treatment of water, such as a biological treatment plant, or an oxidizing treatment. This bleed will be greater or lesser according to the amount of water which is carried along in the acrolein-enriched phase (9). The water bleed can advantageously be carried out at the device (G), by allowing a suitable amount of water to leave with the organic by-products heavier than water in the stream (18).

According to one embodiment of the invention, the stream (6a) originating from the device (C) can be reinjected into the stream (10) upstream of the device (G) or in a mixing stage (A) upstream of the unit (K), so as to recycle the unconverted glycerol in the dehydration reactor (B). Under these conditions, the heavy products separated from the stream (6) by the unit (C) will be effectively removed from the water loop at the units (G) or (K).

According to one embodiment of the process according to the invention (not represented in FIG. 1), the acrolein-enriched phase (9), which is freed from the heavy by-products and from a large part of the water, originating from stage b) for separation of the stream resulting from the dehydration stage a) is subjected to a purification treatment comprising absorption/distillation stages, such as those described, for example, for the acrolein stream produced by oxidation of propylene in the document Techniques de l'Ingénieur, Traité Génie des Precédés [Engineering Technologies, Process Engineering Treatise], J 6 100 1-4.

The purification of the stream (9) comprising the acrolein, after cooling by one or more heat exchangers, generally comprises an absorption in water or a recycled aqueous stream to allow the noncondensable products to leave at the top and to recover, at the bottom, a dilute aqueous solution of acrolein.

This absorption, can be carried out in a packed or plate column, preferably countercurrentwise. Advantageously, the noncondensable light compounds, such as nitrogen, oxygen, carbon monoxide and carbon dioxide, are removed at the top of the column.

The aqueous acrolein solution is subsequently separated by distillation. For this, use may be made of a sequence of distillation columns, as described, for example, in U.S. Pat. No. 3,433,840, or a single column, as described, for example, in the documents EP 1 300 384 or EP 1 474 374. This distillation makes it possible to recover, on the one hand, a stream predominantly composed of water, most of which is generally recycled to the absorption stage, and, on the other hand, a gas or liquid stream comprising a content by weight of acrolein of greater than 80% and preferably >94% and a content by weight of water of less than 15%, with respect to the acrolein, preferably <5%.

The stream (9) comprising acrolein can also be purified simply by distillation without prior absorption in water. This alternative is advantageously employed when the stream (9) comprises little in the way of noncondensable gases.

The liquid or gaseous acrolein stream, obtained on conclusion of the stages for purification of the stream (9), can then be used to prepare methylmercaptopropionaldehyde (MMP) by reaction with methyl mercaptan in the presence of a catalyst. The reaction of MMP, optionally purified, with hydrocyanic acid or sodium cyanide, carried out according to the Bücherer or Strecker synthesis well known to a person skilled in the art, then results either in methionine or in the hydroxy analogue of methionine, after conversion of the reaction product, as described in the document Techniques de l'Iingénieur, Traité Génie des Procédés, J 6 410-4 to 9.

Manufacture of Acrylic Acid

Figure 2:
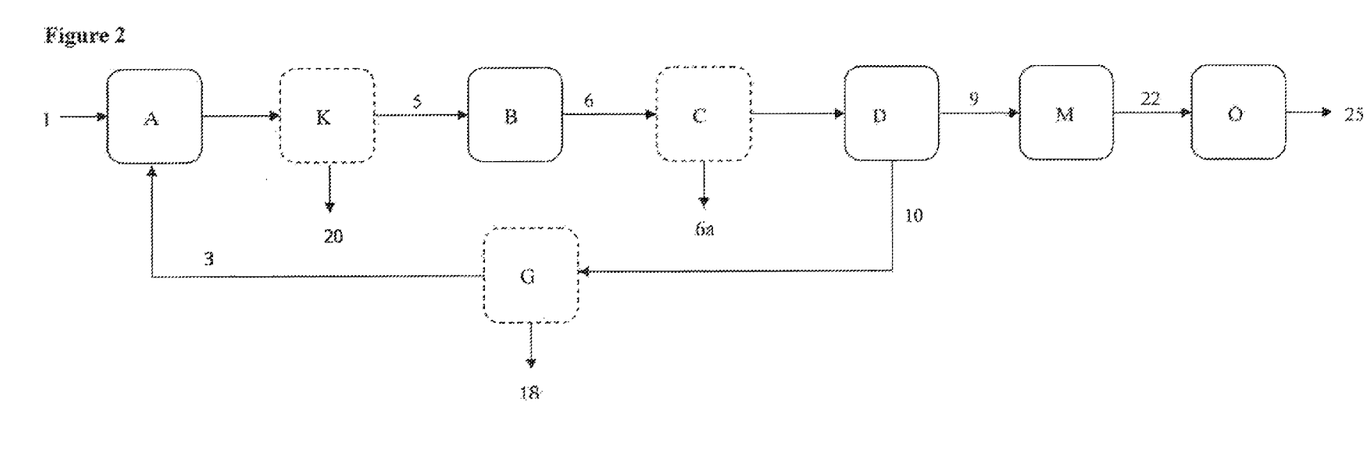
FIG. 2: block diagram of the process for the manufacture of acrylic acid according to the invention, in which the stage of separation of heavy by-products by difference in boiling point is represented in dotted lines.

With reference to FIG. 2, for the implementation of a process according to the invention, the phase (9) enriched in acrolein and freed from the heavy by-products and from a large part of the water, originating from stage b) for separation of the stream resulting from the dehydration stage a), is subjected to a catalytic oxidation reaction d) in a reactor (M) in order to Obtain a stream (22) comprising the desired acrylic acid. This stream is subsequently subjected, in a stage e), to one or more purification treatments (O), making it possible to recover purified acrylic acid (25).

The reaction for the oxidation of the acrolein to give acrylic acid is carried out in the presence of molecular oxygen or of a mixture comprising molecular oxygen, at a temperature ranging from 200° C. to 350° C., preferably from 250° C. to 320° C., and under a pressure ranging from 1 to 5 bar, in the presence of an oxidation catalyst. Use is made, as oxidation catalyst, of all types of catalysts well known to a person skilled in the art for this reaction. Use is generally made of solids comprising at least one element chosen from the list Mo, V, W, Re, Cr, Mn, Fe, Co, Ni, Cu, Zn, Sn, Te, Sb, Bi, Pt, Pd, Ru and Rh, present in the metallic form or in the oxide, sulphate or phosphate form. Use is made in particular of the formulations comprising Mo and/or V and/or W and/or Cu and/or Sb and/or Fe as main constituents.

The oxidation reactor (M) can operate as a fixed bed, as a fluidized or as a circulating fluidized bed. It is also possible to use a plate exchanger with a modular arrangement of the catalyst, such as described in the documents EP 995 491, EP 1 147 807 or US 2005/0020851.

The gas mixture (22) resulting from the oxidation reaction is composed, apart from the acrylic acid, of various compounds, such as:

light compounds which are noncondensable under the temperature and pressure conditions normally employed: $N_2$, unconverted $O_2$, CO and $CO_2$, formed in a small amount by the last oxidation or going around, by recycling, in the process, condensable light compounds, in particular the residual water from the preceding stage, generated by the dehydration reaction or present as diluent, unconverted acrolein, light aldehydes, such as formaldehyde and acetaldehyde, formic acid, acetic acid and propionic acid, residual heavy compounds from the preceding stage: furfuraldehyde, benzaldehyde, maleic acid, maleic anhydride, benzoic acid, phenol or protoanemonin.

Figure 3:
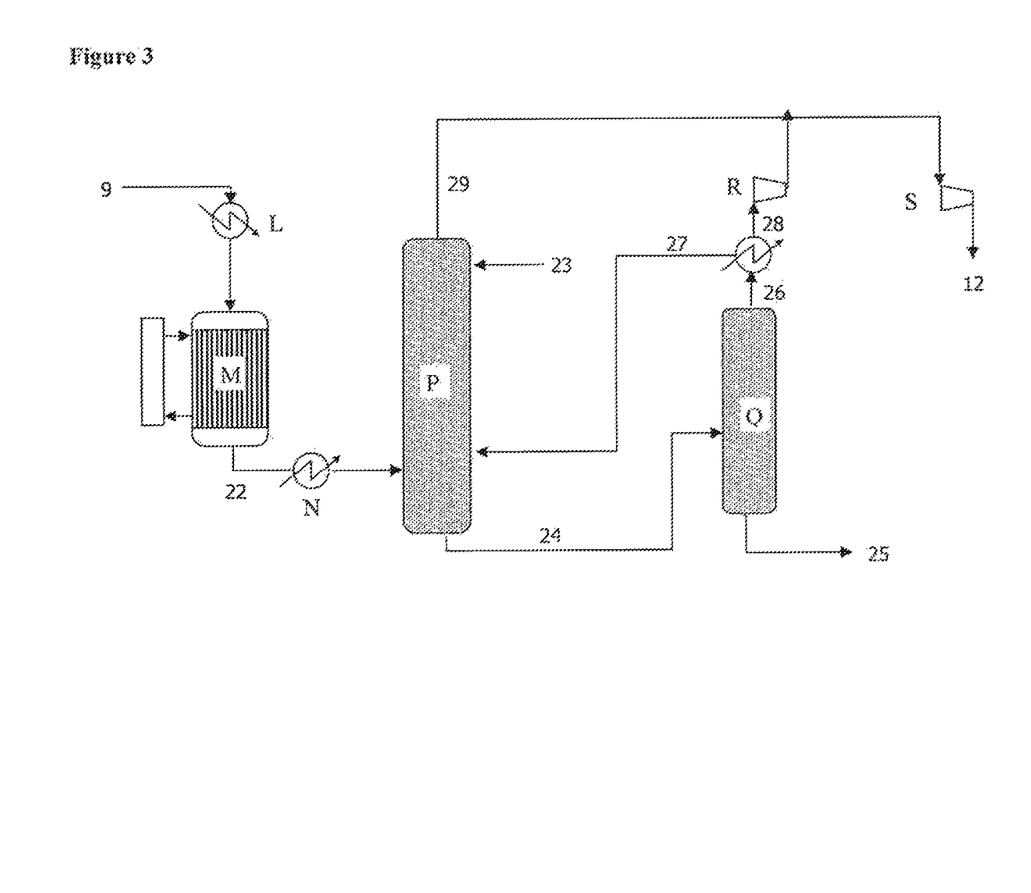
FIG. 3: detailed diagram of stages d) and e) of the process for the manufacture of acrylic acid according to the invention.

In order to obtain acrylic acid corresponding to a certain technical grade, it is necessary to subject this mixture (22) to a recovery/purification sequence represented in part, for example, in FIG. 3:

The first stage of this purification phase consists of an extraction of acrylic acid by countercurrentwise absorption. For this, the gas mixture (22), optionally after cooling in an exchanger (N), is introduced at the bottom of an absorption column (P), where it encounters, countercurrentwise, a solvent (23) introduced at the column top, generally water. The light compounds which are noncondensable under the temperature and pressure conditions normally employed (respectively more than 50° C. and less than $2 \times 10^5$ Pa) are removed at the top of this absorption column in a stream (29). The solvent (23) employed in this column is water. The water might be replaced by a hydrophobic solvent with a high boiling point, as described, for example, in BASF Patents FR. 2 146 386 and U.S. Pat. No. 5,426,221, and also in Patent FR 96.14397, The water used as absorbing solvent can be contributed by a source external to the process but can be composed, in all or in part, of water resulting from the recycling of an aqueous phase in the process, for example the water separated in the separating unit (D) or the water recovered from the top stream of an azeotropic drying column optionally present in the purification sequence. According to an alternative form, water external to the process is not added in the absorption column The operating conditions of this absorption stage are as follows:

The gaseous reaction mixture is introduced at the column bottom at a temperature of between 130° C. and 250° C. The water is introduced at the column top at a temperature of between 10° C. and 60"C. The respective amounts of water and of gaseous reaction mixture are such that the water/acrylic acid ratio by weight is between 1/1 and 1/4. The operation is carried out at atmospheric pressure.

The absorption colunm (P) can be coupled to a column for the distillation of the very light compounds, essentially acrolein unconverted on conclusion of the reaction which is present at a low concentration in the aqueous acrylic acid solution recovered at the bottom of the absorption column. This distillation column (Q), which operates under a pressure of $6 \times 10^3$ to $7 \times 10^4$ Pa, is fed at the top by the stream (24) from the bottom of the preceding absorption column and makes it possible to remove, at the top, a stream (26) of acrolein-enriched acrylic acid which is at least partially recycled, via a condenser, in the from of a liquid stream (27), at the lower part of the absorption column, for final removal at the top of this same column, the remaining gas stream (28) being recompressed in a compressor (S) and optionally conveyed to the oxidizer present in the process or else is recycled in the dehydration reactor (B) or to the separation stage (D). There is thus obtained, on conclusion of these purification stages, a mixture (25) of acrylic acid in the solvent, preferably in water, (ratio by weight 1/4 to 4/1) freed from the bulk of the unconverted acrolein, which is referred to as "crude acrylic acid".

According to the grade desired for acrylic acid, this mixture will be subjected to additional treatments described in numerous patents, in particular to a dehydration stage which is carried out in the presence of a water-immiscible solvent for acrylic acid. This dehydration stage can be carried out by azeotropic distillation of the solvent, water and acrylic acid mixture, which makes it possible to take out the solvent/water azeotrope at the distillation top. The acrylic acid recovered at the bottom is subsequently subjected to distillation of the light compounds (topping) and separation of the heavy compounds (tailing). A grade of acrylic acid referred to as "technical" is then obtained, which grade can then be subjected to a subsequent purification, for example by fractional distillation, to give a glacial grade.

Examples of the purification of acrylic acid have been described in patent application WO 10/31949, FR 09.55111, FR 09.55112 or FR 10.51961.

Figure 4:
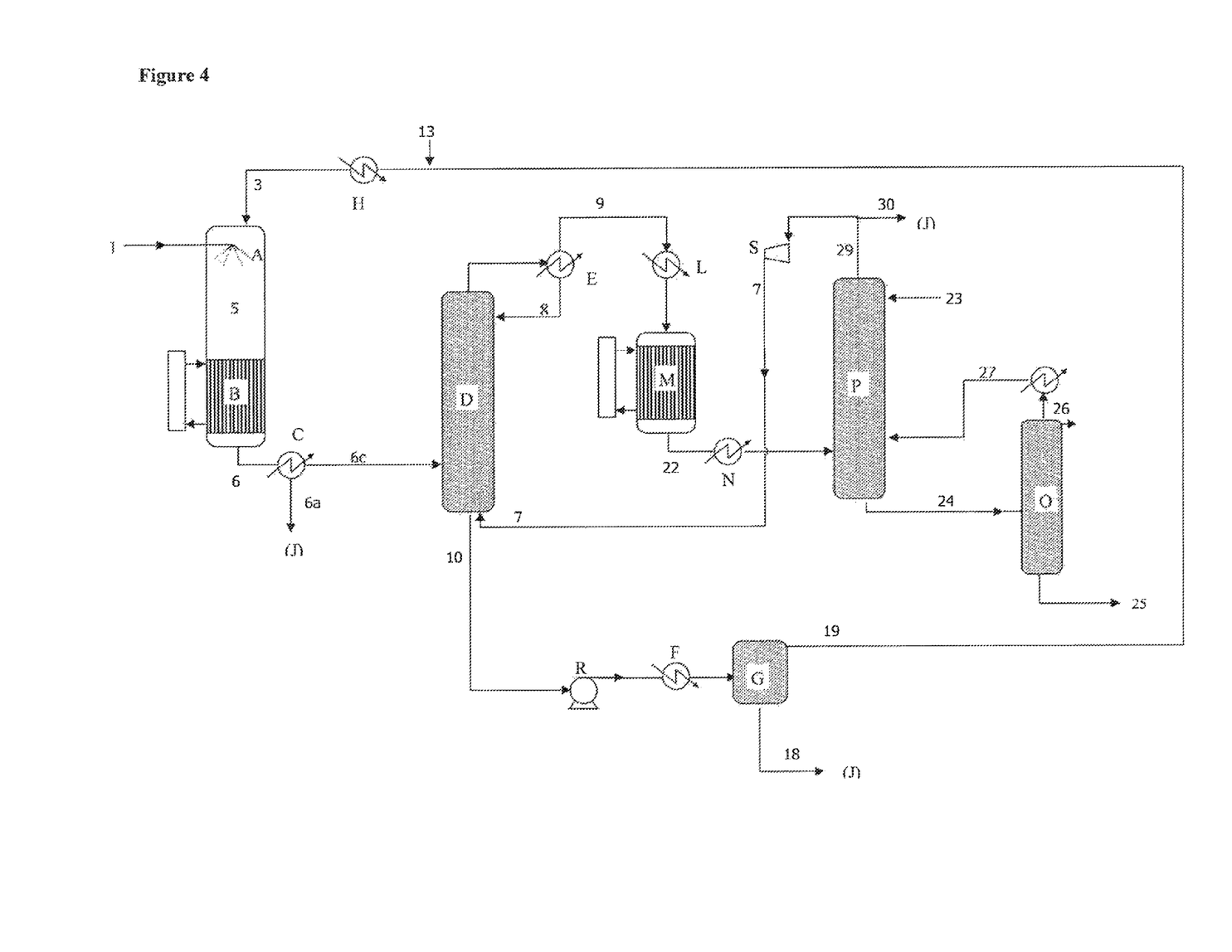
FIG. 4: detailed diagram of a preferred embodiment of the process for the manufacture of acrylic acid according to the invention.

According to a preferred embodiment of the process for the manufacture of acrylic acid according to the invention, the reaction for the dehydration of glycerol is carried out in the gas phase and a stage of separation of heavy by-products by difference in boiling points is applied to the aqueous stream exiting from stage a) and to the acrolein-poor aqueous phase of stage b). This embodiment is illustrated, for example, by FIG. 4:

The gaseous stream (5) feeding the dehydration reactor (B) is obtained in the mixing chamber (A), in which the glycerol is evaporated using hot gases resulting from the recycling (3) of the aqueous phase (19) resulting from the unit (G), after removal of the heavy impurities (18) present in the acrolein-poor stream (10) exiting at the bottom of the separating unit (D). The stream (1) of glycerol in the liquid form, optionally preheated to a temperature of the order of 100° C. to 250° C., can be injected into this chamber in a cocurrentwise or countercurrentwise gas flow via spray or atomization nozzles which make it possible to form fine droplets on contact with the recycled stream (3) essentially comprising water, oxygen and $CO_2$ and optionally nitrogen and CO. The spray nozzles make it possible to disperse the stream of liquid glycerol in the form of fine droplets by varying the mechanical effects (size and shape of the orifice of the nozzle, flow rate, pressure). These systems make it possible to form droplets with a size of less than one mm and preferably of less than 300 μm. The finer the size of the droplets, the faster the evaporation of the stream (1). In the scheme of FIG. 4, the energy necessary to preheat the stream (5) entering the reactor is contributed by the superheated stream (3). Alternatively, a heat exchanger might be placed between the mixing unit (A) and the reactor (B).

Oxygen, air or a gas comprising oxygen, which promotes the dehydration reaction, is supplied via a stream (13) or directly into the mixing chamber (A).

The gaseous reaction stream (6) is cooled, at the outlet of the reactor, in a heat exchanger (C) to a temperature of between 120° C. and 180° C., preferably between 140° C. and 170° C., in order to form a liquid stream (6a) of heavy products and a gas stream (6c) which is conveyed to a condensation column (D), equipped with a condenser (E) which makes it possible to separate, on the one hand, a liquid phase (8) predominantly comprising water and acrolein, which is recycled to the column (D), and, on the other hand, the gas stream (9) comprising the acrolein produced. Generally, this stream (9) comprises water in an acrolein/water ratio by weight ranging from 1/0.02 to 1/3 and preferably from 1/0.5 to 1/2 but also the light by-products, such as acetaldehyde, propionaldehyde, acetone and optionally $O_2$ and inert gases nitrogen, CO and $CO_2$. n order to strip acrolein from the liquid stream (10) exiting at the bottom of the column (D), the latter can be fed at the bottom with a gas stream (7) resulting from the top of the column (P) for the absorption of acrylic acid in water. Alternatively, the stripping of the acrolein can be carried out by reboiling at the bottom of the column (D) or by the addition of a stripping column fed at the top by the liquid stream (10) and at the bottom by a gas stream as described above.

The liquid stream (10) exiting at the bottom of the absorption column (D) is pumped into the exchanger (F) to bring it to a temperature ranging from 100° C. to 180° C., preferably from 110° C. to 150° C., under a pressure of 1 to 5 bar, and then conveyed to the unit (G) in order to be subjected to evaporation. The liquid evaporation residue (18), concentrated in organic compounds which are heavier than water, is either injected into an oxidizer (J) or eliminated from the process and treated by any means known to a person skilled in the art. The gas phase (19), which mainly comprises water with a small amount of light by-products, is mixed with a stream of air (13) and brought, by virtue of the exchanger (H), to a temperature ranging from 350° C. to 550° C. and preferably from 400° C. to 500° C.

The gas stream (9) comprising the acrolein produced is reheated, by an exchanger (L), to a temperature which can range from 160° C. to 300° C. and then injected into a second fixed-bed multitubular reactor (M) comprising a catalyst for the oxidation of acrolein and a bath of molten salts for removing the heat given off by the reaction.

At the outlet of this reactor, the gas stream (22) is subjected to a recovery/purification sequence as described above using the absorption column (P) and the distillation column (Q). Part of the gas phase (29) exiting at the top of the column (P) is recompressed by the compressor (S) to form the stream (7), which is returned to the column (D), it being possible for the other part (30) to be conveyed to a thermal oxidizer (J).

For energy optimization of the process, the flue gases from the thermal oxidizer (J) are used as hot fluid for the heat exchangers and in particular for the exchanger (H).

According to another preferred embodiment of the process for the manufacture of acrylic acid according to the invention, the reaction for the dehydration of glycerol is carried out in the gas phase and a stage of separation of heavy by-products by difference in boiling points is applied to the stream entering the dehydration stage a) and to the aqueous stream exiting from stage a). This embodiment is illustrated in Example 2 of the experimental part.

Energy Optimization of the Process According to the Invention

Gas streams which have to be cooled and condensed and liquid streams which have to be evaporated are present in the process according to the invention. The use of compression systems, such as heat pumps, or compressions on some streams of the process makes it possible to minimize the heat lost by making it possible to transfer heat from the coolest medium to the hottest medium. The heat pump is a thermodynamic device, the operation of which is based on the principle of the compression cycle of refrigerants. When the refrigerant is compressed and passes from the gas state to the liquid state, an exothermic (condensation) phenomenon occurs which produces heat. Conversely, if the refrigerant is reduced in pressure, bringing it from the liquid state to the gas state, an endothermic (evaporation) phenomenon occurs which makes it possible to absorb heat and to cool down. Everything is based on the change in state used in a closed circuit.

In the process of the invention, use is advantageously made of a heat pump to recover the energy of condensation of the water of the gaseous reaction stream (6c) at the outlet of the dehydration reactor and to evaporate the aqueous phase depleted in acrolein separated from the phase enriched in acrolein during stage b). The heat pump can operate with water or with any suitable refrigerant known to a person skilled in the art, such as, for example, 1,1,1,3,3-pentafluoropropane or 1,1,1,3,3-pentafluoropentane, or a composition comprising at least one hydrochloroolefin, such as 1.-chloro-3,3,3-trifluoropropene or 2-chloro-3,3,3-trifluoropropene, or a composition comprising, by weight, from I to 50% of methyltetrahydrofuran and from 5 to 99% of nonafluorobutyl alkyl ether of formula $C_4F_9OR$, R comprising from 1 to 4 carbon atoms, such as described in Patent Application FR 2 928 648.

In the case where the dehydration reaction is carried out in the gas phase, the stream (6) exits from the reactor in the form of a gas mixture at a temperature ranging from 150° C. to 550° C. and preferably between 250° C. and 400° C. This stream is cooled by virtue of a first heat exchanger (not represented) in order to bring it to a temperature ranging from 150° C. to 200° C. Generally, this exchanger makes it possible to recover energy by producing low-pressure steam. A second exchanger makes it possible to cool this stream to a temperature ranging from 70° C. to 120° C. and preferably from 90° C. to 110° C., either at the inlet (exchanger (C)) or at the top of the absorption column (D) (exchanger (E)), from where the liquid phase depleted in acrolein (10), separated from the gas phase enriched in acrolein (9), exits at the bottom. This liquid stream (10) is evaporated at a pressure greater by 0.1 to 3 bar than the inlet pressure of the dehydration reactor by virtue of the unit (G) at a temperature ranging from 100° C. to 180° C. and preferably from 110° C. to 150° C.

The heat pump operating with a refrigerant which can be water or any other refrigerant is installed on the abovementioned second heat exchanger and the abovementioned heat exchangers of the unit (G). A liquid stream is evaporated in the first exchanger and then compressed in a compressor at a pressure of between 2 and 30 bar and preferably from 2 to 8 bar at a temperature of 110° C. to 200° C. The stream obtained is condensed in the second heat exchanger and then reduced in pressure and cooled in order to restore the liquid stream, thus forming a loop between the two exchangers.

In the case where the dehydration reaction is carried out in the gas phase, compression systems which make possible recovery of energy can also be used between. the dehydration reaction stage a) and the separation stage b), so as to be able to recover the energy of condensation of the water present in the gaseous reaction stream during the separation stage b). In a configuration exemplified by FIG. 4, the gas stream (6) exiting from the dehydration reactor is cooled by the heat exchanger (C) and then recompressed by a compressor (not represented in FIG. 4) before being injected into the condensation column (D). The column (D) and the exchanger (E) operate at a pressure greater by at least 1 bar and preferably at least 2 bar than that of the reactor (B). The liquid stream (10) recovered at the bottom is subsequently evaporated via the exchanger (F) and the unit (G), which operate at a pressure lower than that of the column (D) and (E) by at least 0.5 bar and preferably by at least 1.5 bar and a pressure greater than that of the reactor (B). The compression carried out between stage a) for the dehydration of the glycerol and stage h) can also be carried out by a succession of cooling exchangers and compressors in series.

Under these conditions, the condensation at the top of the column (D) is at a sufficient thermal level for the energy of condensation to be able to he recovered. This condensation at the top of the column (D) can be coupled to the evaporation at the outlet of the pump (R), that is to say that the gas stream exiting at the top of the column can be cooled directly by the liquid stream exiting from the pump (R), which will itself he reheated. In other words, exchangers (C), (E) and (F) and those of the units (G) can be the same exchangers. In another configuration, the condensation at the top of the column (D) carried out by the exchanger (E) can be used to produce steam which can be used at other places in the process for the production of acrolein or acrylic acid or outside the process.

Advantageously, the gas stream (6) exiting from the dehydration reactor can be cooled by the heat exchanger (C) down to a low temperature, typically of 110° C. to 160° C., so as to produce steam in the exchanger (C), which steam can be used at other places in the process for the production of acrolein or acrylic acid or outside the process.

The heat pump(s) employed in the process according to the invention can also be used to produce steam at a sufficient thermal level for it (them) to have a use in or outside the process.

The process according to the invention thus contributes to reducing the consumption of fuels and the discharge of $CO_2$ to the atmosphere.

The bioresourced acrylic acid obtained according to the process of the invention can be used for the manufacture of homopolymers and copolymers produced by polymerization of acrylic acid and optionally of other unsaturated monomers, for example the manufacture of superabsorbant polymers obtained by polymerization of the said partially neutralized acid or by polymerization of the said acid, followed by partial neutralization of the polyacrylic acid obtained.

The bioresourced acrylic acid obtained according to the process of the invention can also be used for the manufacture of polymers or copolymers by polymerization of the derivatives of the said acid in the ester or amide form.

Experimental Part

A simulation using ASPEN software was used in Examples 1 and 2 to illustrate the process according to the invention. The percentages are expressed as % by weight. The pressures are expressed in bar absolute. The entities having a content of less than 1% will not be mentioned.

EXAMPLE 1

With Reference to FIG. 4

Gas-phase dehydration of glycerol to produce acrolein, which is oxidized to give acrylic acid, and separation of heavy products by condensation immediately after the stage of dehydration of glycerol and separation of heavy products by flash distillation on the water loop.

A liquid stream (1) of glycerol preheated to 220° C. (17.4 T/h, 99.0% glycerol) is injected via a spray nozzle (A) into a recycled gas stream (3) (65.2 T/h, 478° C., 2.8 bar, 63.6% water, 24.7% $N_2$, 7.4% $O_2$, 1.4% acrylic acid, 1.2% acetic acid). Spraying the glycerol as fine droplets allows it to evaporate over a short distance.

The resulting gas steam. (5) (79.2 T/h, 320° C., 2.8 bar, 21.7% glycerol, 49.8% water, 19.3% nitrogen, 5.8% oxygen, 1.3% acrylic acid) is conveyed to a fixed-bed multitubular reactor (B) which comprises 35 $m^3$ of a heterogeneous acid dehydration catalyst and which is coupled to a molten salt bath which makes it possible to remove the heat produced by the reactions. A gas stream (6) exits from this reactor at 320° C. under 1.7 bar (58.2% water, 19.3% $N_2$, 4.6% oxygen, 10.6% acrolein, 1.0% acetaldehyde, 1.5% acrylic acid, 1.1% acetic acid). This stream is cooled to 160° C. in a heat exchanger (C), which makes it possible to recover a liquid stream (6a) of heavy products (68 kg/h) and a gas fraction (6c). The liquid stream is conveyed to a thermal oxidizer (J). The gas fraction is conveyed to an absorption column (D). A gas stream (7) (21.8 T/h., 138° C., 65.3% $N_2$, 22.0% water, 3.7% $CO_2$, 3.1% CO, 2.6% $O_2$) is injected at the bottom of the column (D). The column (D) comprises, at the top, a partial condenser (E). A liquid phase (8) (75° C., 48.4 T/h) exits from this partial condenser (E), which phase is returned to the column (D), and an acrolein-enriched gas stream (9) (54.6 T/h) exits from this partial condenser (E) at 75° C. under 1.7 bar, which gas stream comprises 54.6% $N_2$, 15.6% acrolein, 14.0% water, 7.7% $O_2$, 2,4% $CO_2$, 2.4% CO and 1.6% acetaldehyde.

The gas stream (9) is reheated to 240° C. by an exchanger (L) and then injected into a second fixed-bed multitubular reactor (M) comprising an oxidation catalyst and a bath of molten salts for removing the heat given off by the reaction. At the outlet of this reactor, the gas stream (22) (54.6 T/h, 54.0% $N_2$, 19.0% acrylic acid, 14.3% water, 3.0% $CO_2$, 2.6% carbon monoxide, 2.1% oxygen, 1.5% acetic acid) is cooled to 160° C. by the exchanger (N) and then injected into the absorption column (P). A stream (23) of 6.0 T/h of water is injected at 25° C. at the top of this column A liquid phase (24) is recovered at the bottom, which phase is sent to a column (Q) operating under vacuum which makes it possible to recover a stream of acrylic acid (25) (15.4 T/h, 66.2% acrylic acid, 25.0% water, 5.1% acetic acid, 3.1% formic acid). At the top of the column (Q), the gas stream (2.6) (1.6 T/h, 72° C., 0.3 bar) is conveyed to a condenser and then to the column (P). Part of the gas phase (29) exiting at the top of the column (P) (45.2 T/h, 72° C., 1.1 bar, 65.3% $N_2$, 22.0% water, 3.7% $CO_2$, 3.1% CO, 2.6% $O_2$) is recompressed to 1.8 bar by the compressor (S) and forms the stream (7) described above. The other part (30) is sent to a thermal oxidizer (J).

The acrolein-poor liquid stream (10) exiting at the bottom of the column (D) (46.3 T/h, 86° C., 1.8 bar, 93.4% water, 0.04% acrolein, 1.9% acetic acid, 2.6% acrylic acid, 1.0% hydroxypropanone, 1.1% other heavy organic compounds) is pumped into an exchanger (F), which. brings it to 132° C. under 2.8 bar, and then flash distilled in the flash drum (G), to give a liquid phase (18) (4.6 T/h) and a gas phase (19) (41.7 T/h, 94.3% water, 2.5% acrylic acid, 1.5% acetic acid). This gas phase (19) is mixed with a stream of air (13) of 20.2 T/h at 166° C. under 2.8 bar and then heated to 478° C. to fibrin the stream (3). Heating can be carried out by an exchanger (H), the hot fluid of which is composed of the flue gases from the thermal oxidizer (J).

EXAMPLE 2

Figure 5:
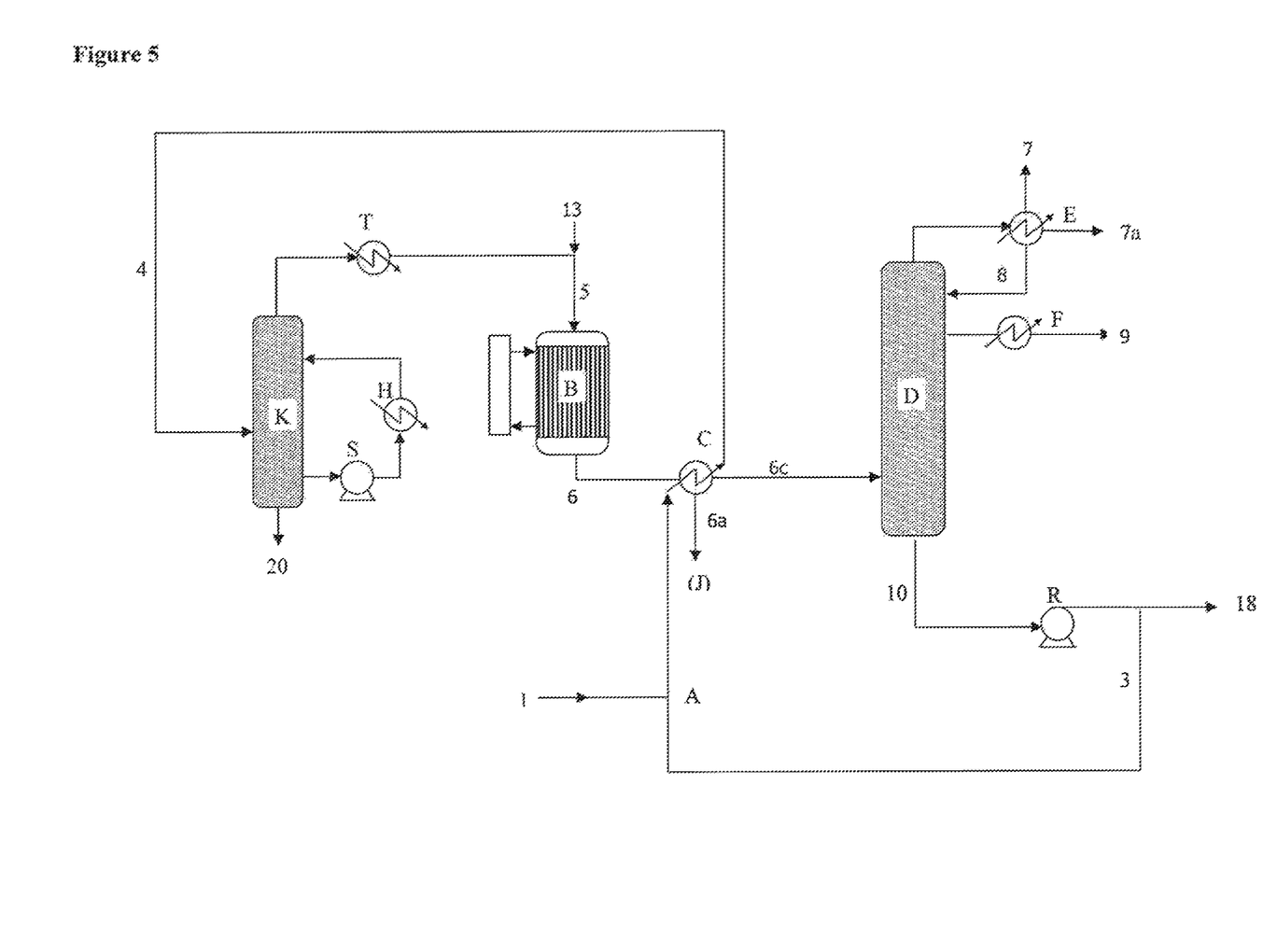
FIG. 5: detailed diagram of a preferred embodiment of the process for the manufacture of acrolein according to the invention.

With Reference to FIG. 5

Gas-phase dehydration of glycerol to produce acrolein comprising a separation of heavy products by flash distillation immediately before the stage of dehydration of the glycerol and a separation of heavy products by condensation immediately after the stage of dehydration of glycerol.

A liquid stream (1) of glycerol at 25° C. (210 kg/h, 99.0% glycerol) and a recycled liquid stream (3) (519 kg/h, 124° C., 93% water, 2.6% acetic acid, 2.1% acrylic acid and 1.0% hydroxypropanone) are mixed in (A), then preheated to 212° C. under 25 bar via the exchangers (C) and then conveyed to a flash distillation column (K) operating under 2.8 bar absolute, which makes it possible to separate the heavy by-products. This column comprises a loop on the liquid phase equipped with a pump (S) and with a heat exchanger (H) intended to contribute the heat necessary for evaporation of the glycerol and the water. A stream of heavy by-products (20) of 3 kg/h at 244° C. is recovered at the bottom of the column (K), which by-products are eliminated. The gas phase exiting at the top of this column (K) is conveyed to an exchanger (T), in order to reheat it to 303° C., and is then mixed with a stream of oxygen (13) (14 kg/h), in order to form the stream (5) (740 kg/h, 2.8 bar absolute, 300° C., 65% water, 28% glycerol, 1.9% oxygen, 1.8% acetic acid, 1.5% acrylic acid), The gas stream (5) is conveyed to a fixed-bed multitubular reactor (B) which comprises a heterogeneous acid dehydration catalyst and which is coupled to a molten salt bath which makes it possible to remove the heat produced by the reactions. A gas stream (6) exits from this reactor at 314° C. (76% water, 13.6% acrolein, 2.1% acetic acid, 1.7% acrylic acid, 1.2% acetaldehyde, 1.0% carbon monoxide).

This stream is cooled to 123° C. in the heat exchangers (C) already described, which make it possible to recover a liquid stream (6a) of heavy products (29 kg/h) and a gas fraction (6c). The liquid stream is sent to a thermal oxidizer (J). The gas fraction is conveyed to an absorption column (D). The column (D) comprises a condenser (E) at the top. A gas phase (7) (26 kg/h, 0° C., 2.3 bar, 29% CO, 22% $CO_2$, 19% acetaldehyde, 18% formaldehyde, 13% $O_2$) is recovered at the top and a liquid phase is recovered at the outlet of the condenser (E), which liquid phase is partially withdrawn (2 kg/h, 0° C., 2.3 bar, 78% acetaldehyde, 15% formaldehyde, 4% acrolein) and partially recycled to the column. A side stream is drawn off from the column and is condensed by means of the exchanger (F) to give a stream (9) of acrolein (109 kg/h, 30° C., 92.2% acrolein, 4.9% water, 2.2% acetaldehyde), The acrolein-poor liquid stream (10) exiting the bottom of the column (D) (574 kg/h, 124° C., 93% water, <0.1% acrolein, 2.6% acetic acid, 2.1% acrylic acid, 1.0% hydroxypropanone) is divided into a stream (18), which is eliminated (55 kg/h), and the stream (3) described above.

EXAMPLE 3

Laboratory Test According to the Invention

An acid dehydration catalyst is prepared by impregnation with the pore volume of an aqueous phosphotungstic acid solution on a titanium oxide reduced to a particle size of 300-500 µm. The catalyst is dried in a ventilated oven at 110° C. and then calcined at 500° C. for 3 hours. A volume of 7 ml of the catalyst is introduced into a reactor made of 316L stainless steel with a diameter of 13 mm placed vertically in an oven heated to 280° C.

A flow rate of 15 g/h of a solution composed of 50% by weight of pure glycerol and 50% of water is mixed with a flow rate of oxygen and nitrogen of 1.2 and 18 standard litres/hour respectively and then conveyed to an evaporator which heats the mixture to 280° C. and which is connected to the reactor.

The gaseous effluents at the outlet of the reactor are either conveyed to two traps in series which initially comprise 120 and 80 grams of water and which are cooled to 0° C., so as to completely trap the acrolein in order to produce a material balance, or are conveyed to a tank cooled to 0° C., so as to trap most of the water and heavy products produced by the reaction. In both cases, the uncondensed gases are eliminated to the atmosphere after washing in a trap comprising a dilute sodium hydroxide solution. The pressure drop in the reactor is measured throughout the experiment.

A material balance was carried out with the traps in series filled with water from the time t=2 hours to t=3 hours 30, on the one hand, and from the time t=21 hours to t22 hours 30. The glycerol and acrolein contents in the traps were measured by gas chromatography. The glycerol conversion and the acrolein yield are calculated according to the formulae:

Glycerol conversion (%)=((moles of glycerol injected into the reactor throughout the duration of the balance)−(moles of glycerol recovered in the 2 traps))/(moles of glycerol injected into the reactor throughout the duration of the balance)*100

Acrolein yield (%)=(moles of acrolein recovered in the 2 traps)/(moles of glycerol injected into the reactor throughout the duration of the balance)*100

The results of the experiment are given in Table 1 below.

Furthermore, most of the water and of the heavy products was collected in the tank between the time t=1 hour and the time t=2 hours and also between the time t=3 hours 30 and the time t=21 hours. This aqueous solution was subsequently treated for 2 hours on a rotary evaporator heated to 30° C. and under partial vacuum, so as to evaporate the acrolein. Collecting in the tank and evaporating make it possible to simulate stage (D) represented in FIG. 1. In order to simulate stage (G) of FIG. 1, the aqueous solution freed from the acrolein is distilled on a rotary evaporator at 75° C. under partial vacuum, so as to recover a condensate of recycled water, on the one hand, and a residue of highly coloured organic products in the distillate, on the other hand.

In order to simulate stages (A) and (B) of FIG. 1, the condensate of recycled water was mixed with glycerol, so as to obtain a 50% glycerol solution, and the experiment for the dehydration of glycerol was repeated. The results are given in Table 1.

When recycled water, which has been subjected to separation of the heavy products by distillation, is used, glycerol conversions and acrolein yields are obtained which are similar to those obtained on using pure water.

EXAMPLE 4

Comparative

In the same way as in Example 3, the reaction for the dehydration of glycerol was carried out with a solution composed of 50% by weight of pure glycerol and 50% of water, and most of the water and of the heavy products was collected in a tank and was treated for 2 hours on a rotary evaporator heated to 30° C. and under partial vacuum, so as to evaporate the acrolein.

The aqueous solution recovered, comprising a mixture of recycled heavy products and water, was then mixed directly with pure glycerol, in order to prepare a 50% glycerol solution, and the experiment for the dehydration of glycerol was repeated. A pressure drop of 0.1 bar over the reactor was observed over 3 hours 30 and then the pressure gradually increased to reach 0.3 bar after 5 hours and to exceed 1 bar after 7 hours. The experiment could not be continued.

The results are given in Table 1.

When use is made of recycled water comprising heavy products, a very rapid rise in pressure was observed as a result of a blockage of the reactor,

TABLE 1

| | Glycerol conversion after 2 h/21 h (%) | Acrolein yield after 2 h/21 h (%) | Pressure drop after 2 h/5 h/ 21 h (bar) |
|---|---|---|---|
| Example 3 Glycerol/water | >99/80 | 70/48 | 0.1/0.1/0.1 |
| Example 3 Glycerol/recycled water condensate | >99/79 | 70/47 | 0.1/0.1/0.1 |
| Example 4, comparative Glycerol/recycled heavy products and water without distillation stage | >99/impossible to measure | 70/impossible to measure | 0.1/0.3/>1 (7 h) |

The invention claimed is:

1. Process for the manufacture of acrolein from glycerol comprising at least the stages of:
    a) subjecting glycerol to a dehydration reaction to obtain an aqueous stream comprising acrolein,
    b) separating the stream resulting from stage a) into an acrolein-rich phase and an acrolein poor aqueous phase,
    c) recycling all or part of the acrolein-poor aqueous phase to stage a), and
    d) separating heavy by-products by difference in boiling point, which separation stage is applied to at least one of the following streams: a stream entering stage a), the aqueous stream exiting from stage a), or the acrolein-poor aqueous phase of stage b).

2. Process according to claim 1, comprising the step of purifying the acrolein-rich phase by absorption and/or distillation.

3. Process according claim 1, characterized in that the stage of separation of the heavy by-products by difference in boiling point is applied to the stream entering stage a) and/or to the acrolein-poor aqueous phase of stage b), and optionally with a stage of separation of heavy by-products by difference in boiling point applied to the aqueous stream exiting from stage a).

4. Process according to claim 1, characterized in that the stage of separation of the heavy by-products is carried out by evaporation when the stream to be separated is initially liquid, by condensation when the stream to be separated is initially gaseous, or by a combination of evaporation and of condensation when several separation stages are used.

5. Process according to claim 1, characterized in that heavy compounds are removed by evaporation of a mixture of glycerol and a recycled water-rich phase to generates a glycerol and water rich phase stream that is depleted of heavy compounds, and a liquid or solid phase rich in organic compounds heavier than water.

6. Process according to claim 1, characterized in that heavy compounds are removed by treating a stream resulting from the dehydration reaction to generate a gas phase that is depleted in manic compounds heavier than water, and a liquid or solid phase enriched in organic compounds heavier than water.

7. Process according to claim 1, characterized in that heavy compounds are removed by evaporating a stream exiting from a separating unit to generate a water-rich gas phase, which is recycled, and a liquid or solid phase enriched in organic compounds heavier than water, which is eliminated.

8. Process according to claim 1, characterized in that the aqueous phase recycled to the dehydration stage a) is in the form of a gas stream that is used to evaporate the glycerol stream in the mixing stage (A) before subjecting the reactive gas stream to dehydration.

9. Process according to claim 8, characterized in that the glycerol stream is injected into a mixing chamber by spraying or atomization.

10. Process according to claim 1, characterized in that stage a) is carried out in the gas phase and wherein a heat pump is used to recover energy of condensation of water of a gaseous reaction stream resulting from stage a) and to evaporate the aqueous phase depleted in acrolein separated from the phase enriched in acrolein during stage b).

11. Process according to claim 1, characterized in that stage a) is carried out in the gas phase and a gas stream resulting from stage a) is compressed to recover the energy of condensation of water from the reaction stream during stage b).

* * * * *